United States Patent [19]

Imanaka et al.

[11] Patent Number: 5,686,379
[45] Date of Patent: Nov. 11, 1997

[54] ALKOXYLATION CATALYST, PROCESS FOR THE PREPARATION OF THE CATALYST AND PROCESS FOR PREPARING ALKOXYLATE WITH THE USE OF THE CATALYST

[75] Inventors: Tatsuhiro Imanaka; Toshihiro Tanaka; Jun Kono; Hiroshi Nagumo; Hiroyuki Tamaura, all of Wakayama, Japan

[73] Assignee: Kao Corporation, Tokyo, Japan

[21] Appl. No.: 505,286

[22] PCT Filed: Dec. 14, 1994

[86] PCT No.: PCT/JP94/02098

§ 371 Date: Aug. 21, 1995

§ 102(e) Date: Aug. 21, 1995

[87] PCT Pub. No.: WO95/17248

PCT Pub. Date: Jun. 29, 1995

[30] Foreign Application Priority Data

Dec. 22, 1993 [JP] Japan .................. 5-323883

[51] Int. Cl.[6] .................. B01J 21/10; C07D 295/00
[52] U.S. Cl. .................. 502/340; 502/306; 502/343; 502/353; 568/617; 568/618; 568/620

[58] Field of Search .................. 568/617, 618, 568/620; 502/342, 343, 306, 307, 308, 309, 310, 340, 353; 560/93, 200

[56] References Cited

U.S. PATENT DOCUMENTS

| | | | |
|---|---|---|---|
| 4,375,564 | 3/1983 | Edwards | 568/618 |
| 5,104,987 | 4/1992 | King | 544/401 |
| 5,112,788 | 5/1992 | King | 502/162 |
| 5,191,104 | 3/1993 | King | 558/260 |

*Primary Examiner*—Elizabeth D. Wood
*Assistant Examiner*—Bekir L. Yildirim
*Attorney, Agent, or Firm*—Oblon, Spivak, McClelland, Maier, & Neustadt, P.C.

[57] ABSTRACT

An alkoxylation catalyst comprising metal oxides, having a basicity point expressed in pKa value from 9 to 25 and an acidity point expressed in the amount of ammonia gas adsorbed from 50 to 500 µmol/g, and a process for preparing an alkoxylate with the use of this catalyst. According to the present invention, an alkoxylate having a distribution of the number of moles of alkylene oxide added within a narrow range can be prepared and the reaction product is little contaminated with unreacted starting material and by-products. Further, the catalyst can easily be eliminated from the reaction product.

11 Claims, 2 Drawing Sheets

ALKOXYLATION CATALYST, PROCESS FOR THE PREPARATION OF THE CATALYST AND PROCESS FOR PREPARING ALKOXYLATE WITH THE USE OF THE CATALYST

This application is a 371 of PCT/3P94/02098 Dec. 14, 1994.

BACKGROUND OF THE INVENTION

1. Field of the Invention

The present invention relates to an alkoxylation catalyst, a process for the preparation of the catalyst and a process for preparing an alkoxylate with the use of the catalyst. More particularly, it relates to an alkoxylation catalyst which comprises metal oxides having specific physical properties or chemical composition and a process for the preparation of the catalyst, and a process for preparing an alkoxylate with the use of the catalyst whereby an alkoxylate having a distribution of the number of moles of alkylene oxide added within an extremely narrow range can be prepared with a reduced amount of by-products formed.

2. Description of the Background

Alkylene oxide adducts of compounds containing an active hydrogen atom(s) such as higher alcohols, alkylphenols, primary and secondary alkylamines and fatty acids are useful as surfactants to be incorporated into shampoos, cleansers for tableware, house cleansers, etc. Alternatively, they are also useful as intermediates for the production of the corresponding anionic surfactants through sulfation or carboxymethylation or as intermediates for the production of other industrial products.

The reaction for the addition of an alkylene oxide to a compound containing an active hydrogen atom(s) is usually effected in the presence of an acid catalyst or a base catalyst. Examples of the acid catalysts which have been generally used for this purpose include halides of boric acid, tin, antimony, iron, aluminum, etc., salts of mineral acids such as phosphoric acid and sulfuric acid and metal salts of carboxylic acids such as acetic acid, oxalic acid and carbonic acid. Examples of the base catalyst therefor include hydroxides and alkoxides of alkali metals and lower amines such as diethylamine and triethylamine.

The use of the above-mentioned base catalysts in the preparation of alkylene oxide adducts causes problems because only products having a wide distribution in the number of moles of alkylene oxide added over a wide range can be obtained and the reaction product has a smell due to the starting compound containing an active hydrogen atom (s) remaining therein. Further, the reaction product contains a large amount of adducts having a large number of moles of alkylene oxide added. Therefore, there is another problem that the reaction product has excessively high hydrophilic properties and may not exhibit the desired performance as a surfactant.

When the above-mentioned common acid catalysts are used in the preparation of alkylene oxide adducts, the amount of the starting compound containing an active hydrogen atom(s) remaining in the reaction product can be reduced. In this case, however, by-products such as dioxane and polyalkylene glycols, which are not desirable for attaining high qualities, are formed in large amounts. In addition, such an acid catalyst exerts a corrosive action on metals, which brings about another problem, i.e., the necessity for heavily equipped reaction facilities.

It has been disclosed that when the reaction for the addition of ethylene oxide or propylene oxide to a compound containing an active hydrogen atom(s) is effected with the use of a certain catalyst, the obtained alkoxylate has a distribution of the number of moles of alkylene oxide added within a narrow range.

As such catalysts, there have been proposed, for example, oxide and hydroxide of barium, oxide and hydroxide of strontium, calcium compounds, fired hydrotalcite containing magnesium and aluminum as the main components (see Australian Patent Publication-A No. 89-33349, published on Oct. 26, 1989) and magnesium oxide containing. Al, Ga, Ca, Sc, etc. added (see U.S. Pat. No. 5,012,012, published on Apr. 30, 1991; Assignee: LION CORP.).

It is also known that reaction products which are obtained by using these catalysts and have a distribution of the number of moles of alkylene oxide added within a narrow range are advantageous in physical properties and qualities, for example, flow point, solubility in water and odor, from the viewpoint of the application as a surfactant.

Reaction products obtained by using such catalysts are comparable, with respect to the range of distribution of moles of alkylene oxide added, to the products prepared by using acid catalysts and are less contaminated with unreacted starting material. However, a large amount of by-products including a polyalkylene glycol are formed in this case, since the above-mentioned catalysts have catalytic properties similar to those of the acid catalysts. The use of such catalysts is also disadvantageous in that they can hardly be eliminated from the reaction product via filtration, which is an important factor from an industrial viewpoint.

It is an object of the present invention to solve these problems encountering in the use of the conventional catalysts to thereby provide a catalyst by which an alkoxylate having a distribution of the number of moles of alkylene oxide added within a narrow range and excellent qualities can be prepared and which is usable industrially, a process for the preparation of this catalyst and a process for the preparation of an alkoxylate with the use of this catalyst.

DISCLOSURE OF THE INVENTION

Summary of the Invention

The present inventors have conducted extensive studies on an alkoxylation catalyst which can be appropriately used in the preparation of an alkoxylate with excellent qualities by the addition reaction of an alkylene oxide with a compound containing an active hydrogen atom(s). As a result of these studies, they have found that when a catalyst having both a specific basicity point and a specific acidity point, more particularly specific metal oxides comprising magnesium as the main component, is used, an alkoxylate having a distribution of the number of moles of alkylene oxide added within a narrow range and being extremely little contaminated with unreacted starting material and by-products, which cannot be obtained by using the previously known catalysts, can be prepared at a high reaction rate. Also, the catalyst can very easily be eliminated from the reaction product. The present invention has been completed on the basis of these findings.

Thus, the present invention provides an alkoxylation catalyst comprising metal oxides, having a basicity point expressed in pKa value from 9 to 25 and an acidity point expressed in the amount of ammonia gas adsorbed from 50 to 500 μmol/g, particularly, an alkoxylation catalyst comprising magnesium oxide and a second oxide of at least one element selected from the group consisting of the group 2B elements, the group 4A elements, the group 4B elements, the group 5B elements and the group 6A elements in the periodic table of the subgroup system.

Further, the present invention provides a use of metal oxides, of which the basicity point expressed in pKa value is from 9 to 25 and of which the acidity point expressed in the amount of ammonia gas adsorbed is 50 to 500 μmol/g, as an alkoxylation catalyst.

Furthermore, the present invention provides a process for the preparation of the above-mentioned alkoxylation catalyst, which comprises coprecipitating a water-soluble or water-dispersible magnesium compound with a water-soluble or water-dispersible compound containing at least one element selected from the group consisting of the group 2B elements, the group 4A elements, the group 4B elements, the group 5B elements and the group 6A elements in the periodic table of the subgroup system and firing the precipitate thus obtained.

In addition, the present invention provides a process for preparing an alkoxylate which comprises conducting a reaction for adding an alkylene oxide to a compound containing an active hydrogen atom(s) in the presence of the above-mentioned alkoxylation catalyst.

Further scope and applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

The first feature of the alkoxylation catalyst according to the present invention resides in that it has basic properties for activating a compound containing an active hydrogen atom(s) simultaneously with acidic properties for activating an alkylene oxide. Because of having these properties in a well-balanced state, the alkoxylation catalyst of the present invention has a high reactivity and can give a reaction product which has a distribution of the number of moles of alkylene oxide added within a narrow range and is reduced in the amount of by-products.

An excessively low base strength causes a low catalytic activity. When the base strength is excessively high, on the contrary, the obtained alkoxylate has a distribution of the number of moles of alkylene oxide added over an enlarged range. Therefore, the optimum base strength is pKa 9 to 25, preferably pKa 9 to 18 and particularly preferably pKa 9.3 to 15.0. Further, as a catalyst of the present invention, those having a base strength of pKa 10 to 25 are desirable, those having a base strength of pKa 14 to 18 are still more desirable, and those having a base strength of pKa 15.0 to 17.5 are particularly desirable.

When the acid strength is excessively low, no catalytic activity is exhibited. On the contrary, an excessively high acid strength causes an increase in the amount of by-products such as dioxane and polyethylene glycol thus formed. Therefore, the acid strength, which is expressed in the amount of ammonia gas adsorbed to 1 g of the catalyst (i.e., metal oxides) determined by the ammonia gas adsorption method, ranges from 50 to 500 μmol, preferably from 50 to 250 μmol and still more preferably from 60 to 200 μmol. Further, as a catalyst of the present invention, those having an acid strength of 100 to 400 μmol are desirable, and those having an acid strength of 100 to 250 μmol are still more desirable.

The pKa value representing the basicity point of the metal oxide indicates the ability of the basic sites present on the surface of the catalyst to accept protons from an acid or the ability thereof to donate electron pairs. The base strength of the metal oxide can be measured by using various indicators with known pKa values. When a metal oxide turns the color of an indicator with a higher pKa into the basic color, then the metal oxide has a larger base strength. The basicity point of the metal oxide can be readily determined by the method described in the following examples.

The amount of ammonia gas adsorbed representing the acidity point of the metal oxide is a value determined by causing the metal oxide to adsorb ammonia on the surface thereof in a gas phase and calculating the amount of the ammonia gas thus adsorbed thereon per unit weight (g) of the metal oxide. The acidity point of the metal oxide can be readily determined by the method described in the following examples.

Examples of metal oxides to be used in the present invention which have both a basicity point and an acidity point as specified above are metal oxides comprising magnesium as the main component and, added thereto, at least one metal selected from the group consisting of the group 2B elements, the group 4A elements, the group 4B elements, the group 5B elements and the group 6A elements in the periodic table of the subgroup system, in other words, metal oxides comprising magnesium oxide and an oxide of at least one element selected from the group consisting of the group 2B elements, the group 4A elements, the group 4B elements, the group 5B elements and the group 6A elements in the periodic table of the subgroup system.

Particular examples of the group 2B elements, the group 4A elements, the group 4B elements, the group 5B elements and the group 6A elements in the periodic table of the subgroup system to be added to magnesium include zinc, titanium, zirconium, tin, antimony, bismuth, molybdenum and tungsten. By taking the activity, selectivity and filtering characteristics of the catalyst into consideration, it is preferable to use zinc, antimony, tin, titanium or zirconium, particularly preferably antimony, therefor.

In the catalyst of the present invention, at least one element selected from the group consisting of the group 2B elements, the group 4A elements, the group 4B elements, the group 5B elements and the group 6A elements in the periodic table of the subgroup system is contained in a proportion of preferably from 0.005 to 0.4 atom, particularly preferably from 0.01 to 0.3 atom, per atom of magnesium which is the main component.

The catalyst according to the present invention may further contain a trace amount of a third component, so lone as the effects of the present invention are not deteriorated thereby.

The catalyst according to the present invention can be prepared by the publicly known methods which are not particularly restricted. For example, a precipitant is added to an aqueous solution or a slurry of compounds containing the desired metals which are soluble or dispersible in water. Alternatively, a precipitant is added to an aqueous solution or an aqueous dispersion of compounds containing metals capable of serving as catalytic components other than a support in the presence of a support in the form of a fine powder. The precipitate thus obtained by the above coprecipitation method is then washed with water, dried and fired. Alternatively, a support in the form of a fine powder is impregnated with an aqueous solution or an aqueous dispersion of a compound containing metals capable of serving as catalytic components other than the support. Then the catalyst thus supported on the support is dried and fired. Thus the catalyst of the present invention is prepared.

When the catalyst to be prepared is one supported on a support, examples of the support usable therefor include diatomaceous earth, zeolite, mordenite, montmorillonite, tin oxide, titanium oxide and activated carbon. The amount of the active metal oxide to be supported on the support desirably ranges from 10 to 80% by weight based on the weight of the support.

Examples of the water-soluble or water-dispersible magnesium compound to be used in the preparation of the catalyst include magnesium nitrate, magnesium sulfate, magnesium chloride, magnesium carbonate, magnesium hydroxide and magnesium oxide. Among these magnesium compounds, magnesium nitrate, magnesium sulfate and magnesium chloride may be cited as preferable ones.

Examples of the water-soluble or water-dispersible compound containing at least one element (i.e., a metal) selected from the group consisting of the group 2B elements, the group 4A elements, the group 4B elements, the group 5B elements and the group 6A elements in the periodic table of the subgroup system include nitrates, sulfates, chlorides, carbonates, hydroxides and oxides of these metals. Among these compounds, carbonates, hydroxides and oxides of these metals may be cited as preferable ones, and oxides of these metals may be cited as particularly preferable ones. Further, examples of oxides of these metals include antimony oxides such as diantimony trioxide, diantimony tetroxide and diantimony pentoxide, among which diantimony trioxide is most preferable.

Now the above-mentioned coprecipitation method will be described in greater detail.

First, the water-soluble or water-dispersible magnesium compound and the water-soluble or water-dispersible compound containing at least one element selected from the group consisting of the group 2B elements, the group 4A elements, the group 4B elements, the group 5B elements and the group 6A elements in the periodic table of the subgroup system are dissolved in water to thereby give an aqueous solution or dispersed in water to thereby give a slurry. To the aqueous solution or slurry thus obtained is added an aqueous solution of an alkaline compound selected from the group consisting of ammonia and hydroxides and carbonates of alkali metals, preferably an alkali metal hydroxide, in such an amount that the amount of the alkaline compound is from 0.8 to 1.2 times by molar equivalent as much as the sum of the contents of the magnesium compound and the above-mentioned compound containing, for example, a group 2B element. Thus, the pH value of the resulting mixture is regulated to 6 to 11, preferably 7 to 10. Alternatively, the pH value of the resulting mixture may be regulated to 6 to 8 in some cases.

The obtained mixture is allowed to stand to thereby coprecipitate the hydroxide, carbonate or oxide of magnesium or a mixture thereof, and the hydroxide, carbonate or oxide of, for example, a group 2B metal or a mixture thereof, followed by the recovery of the precipitate. It is also possible to coprecipitate these compounds on a support coexisting therewith. The precipitate thus obtained is washed with water to thereby eliminate the water-soluble compounds. Then, this precipitate is dried and fired at a temperature of 500° to 900° C., preferably 600° to 800° C., desirably under a nitrogen atmosphere.

A preferred embodiment of the impregnation method is as follows.

A water-soluble or water-dispersible magnesium compound and a water-soluble or water-dispersible compound containing at least one element selected from the group consisting of the group 2B elements, the group 4A elements, the group 4B elements, the group 5B elements and the group 6A elements in the periodic table of the subgroup system are dissolved in water to thereby give an aqueous solution or are dispersed in water to thereby give a slurry. Then, a support is introduced into the aqueous solution or slurry obtained above to give a mixture. The mixture thus obtained is stirred to thereby impregnate the support with the aqueous solution or slurry. After recovering the support by filtration, it is dried and fired at a temperature of 500° to 900° C., preferably 600° to 800° C., desirably under a nitrogen atmosphere.

It is also possible that magnesium oxide and an oxide of, for example, a group 2B metal are separately prepared and then mixed with each other at a desired ratio to give a mixture and the mixture is used as the catalyst of the present invention.

The compound containing an active hydrogen atom(s) to be used in the process for the preparation of an alkoxylate according to the present invention is not particularly restricted but may be an arbitrary one, so long as it can be alkoxylated. Examples thereof include alcohols, phenols, polyols, thiols, carboxylic acids, amines, alkanolamides and mixtures thereof.

Examples of the alcohols include higher aliphatic primary alcohols having a saturated or unsaturated linear alkyl group carrying 8 to 22 carbon atoms such as n-octanol, n-decanol, n-dodecanol, n-tetradecanol, n-hexadecanol, n-octadecanol, oleyl alcohol, eicosanol, behenol, nonanol, undecanol and tridecanol, primary alcohols having a branched alkyl group such as 2-ethylhexanol and Guerbet alcohols with 16 to 36 carbon atoms, secondary alcohols such as 2-octanol, 2-decanol and 2-dodecanol, and arylalkyl alcohols such as benzyl alcohol. The Guerbet alcohols are branched-chain alcohols which are synthesized from two molecules of a starting alcohol by condensation reaction through dehydration (the so-called Guerbet reaction).

Examples of the phenols include phenol, p-octylphenol and p-nonylphenol.

Examples of the polyols include ethylene glycol, propylene glycol, diethylene glycol, triethylene glycol, glycerol, sorbitol, trimethylolpropane and pentaerythritol.

Examples of the thiols include primary and secondary thiols such as 1-butanethiol, 1-hexanethiol, 1-octanethiol, 1-decanethiol, 1-dodecanethiol, 2-propanethiol and 2-butanethiol.

Examples of the carboxylic acids include carboxylic acids having a linear or branched, saturated or unsaturated alkyl group such as acetic acid, propionic acid, butyric acid, octanoic acid, lauric acid, myristic acid, palmitic acid, stearic acid, oleic acid, 2-ethylhexanoic acid and isostearic acid and N-acylamino acids.

Examples of the amines include primary and secondary amines having a saturated or unsaturated alkyl group carrying 8 to 36 carbon atoms such as octylamine, dioctylamine, laurylamine, dilaurylamine, stearylamine and distearylamine and polyamines such as ethylenediamine and diethylenetriamine.

Examples of the alkanolamides include laurylmonoethanolamide and lauryldiethanolamide.

Among these compounds containing an active hydrogen atom(s), alcohols having a low acidity are preferable, since the effects of the present invention can be clearly exhibited by using these compounds. Among such alcohols, linear or branched, saturated or unsaturated alcohols carrying 8 to 22 carbon atoms are preferable, and linear or branched, saturated alcohols carrying 10 to 18 carbon atoms are particularly preferable.

The alkylene oxide to be used in the present invention may be an arbitrary one, so long as it can react with a compound containing an active hydrogen atom(s) to thereby form an alkoxylate. It is preferable in the present invention to use ethylene oxide or propylene oxide, which has an oxirane ring, or a mixture thereof.

A preferable embodiment of the process for the preparation of an alkoxylate according to the present invention is as follows. In a reactor such as an autoclave, an alkylene oxide is reacted with a compound containing an active hydrogen atom(s) in the presence of the catalyst of the present invention at a temperature of 80° to 230° C., preferably 120° to 180° C., for 1 to 10 hours. When the reaction temperature is lower than 80° C., the reaction rate cannot attain a sufficient level. On the other hand, a reaction temperature exceeding 230° C. causes decomposition of the product. The catalyst is used in an amount of preferably from 0.01 to 20% by weight and still more preferably from 0.1 to 10% by weight based on the weight of the compound containing an active hydrogen atom(s).

The reaction product thus obtained, in which the catalyst is suspended, may be used as such in some cases. However, the catalyst is usually separated from the reaction product by, for example, filtration or centrifugal separation. When the catalyst according to the present invention is used, an additional advantage thereof, i.e., its remarkably excellent filtering characteristics, can also be observed.

The main factors affecting the filtering characteristics of a catalyst include clogging of filter paper or filter cloth with high-molecular-weight polyalkylene glycols formed as by-products. The formation of these polyalkylene glycols can be considerably suppressed by using such a catalyst as the one of the present invention which has a specific basicity point simultaneously with a specific acidity point. As a result, the catalyst has excellent filtering characteristics when it is to be eliminated from the reaction product. Thus, the catalyst can be completely eliminated from the reaction product by a simple filtering procedure without requiring any troublesome operation such as adsorption and aggregation.

When polyalkylene glycols, which have a high adsorbability on the surface of the catalyst metals, are formed in a large amount as by-products, the recovered catalyst has a seriously lowered activity. However, the process according to the present invention with the use of the catalyst Of the present invention, wherein polyalkylene glycols are formed in only an extremely small amount, is free from this disadvantage. The catalyst of the present invention can be recovered by a simple filtration procedure and reused. Thus, the catalyst of the present invention has excellent characteristics from an industrial viewpoint.

By the process for the preparation of an alkoxylate with the use of the catalyst of the present invention, an alkoxylate which has a distribution of the number of moles of alkylene oxide added within a narrow range and is little contaminated with unreacted starting materials and by-products can be prepared. In addition, the catalyst of the present invention can be easily eliminated from the reaction product. Thus, the present invention is highly valuable in the industry.

EXAMPLES

Now the present invention will be illustrated in more detail by reference to the following Examples. However, they should not be considered to limit the scope of the present invention.

Unless otherwise noted, all percentages given in these examples are by weight.

Example 1

128.21 g (0.5 mol) of magnesium nitrate hexahydrate, 7.44 g (0.025 mol) of zinc nitrate hexahydrate and 258.75 g of deionized water were fed into a reactor. Into the mixture thus obtained was added dropwise 258.75 g (0.525 mol) of a 20% aqueous solution of sodium carbonate at 90° C. for 2 hours. After completion of the dropwise addition, the resulting mixture was maintained at 90° C. for 1 hour. That is, it was aged. The mixture containing a precipitate was filtered to remove the mother liquor. Then the precipitate thus recovered was washed with 1-l portions of deionized water 5 times. The precipitate was dried at 90° C. for a day and then fired at 600° C. in a nitrogen atmosphere for 2 hours. Thus, an MgO—ZnO catalyst [Mg:Zn (atomic ratio) being 1:0.05] was obtained.

Example 2

217.95 g (0.85 mol) of magnesium nitrate hexahydrate, 5.72 g (0.0425 mol) of stannous oxide and 435.16 g of deionized water were fed into a reactor. Into the mixture thus obtained was added dropwise 450.46 g (0.85 mol) of a 20% aqueous solution of sodium carbonate at 90° C. for 2 hours. After completion of the dropwise addition, the resulting mixture was maintained at 90° C. for 1 hour. That is, it was aged. The mixture containing a precipitate was filtered to remove the mother liquor. Then the precipitate thus recovered was washed with 1-l portions of deionized water 5 times. The precipitate was dried at 80° C. for 2 days and then fired at 500° C. in a nitrogen atmosphere for 2 hours. Thus an MgO—SnO catalyst [Mg:Sn (atomic ratio) being 1:0.05] was obtained.

Example 3

128.21 g (0.5 mol) of magnesium nitrate hexahydrate, 20.0 g (0.025 mol) of a 30% aqueous solution of titanium sulfate and 252.59 g of deionized water were fed into a reactor. Into the mixture thus obtained was added dropwise 291.47 g (0.5S mol) of a 20% aqueous solution of sodium carbonate under the same conditions as those of Example 2. Then the same procedure as that of Example 2 was effected to give an MgO—TiO$_2$ catalyst [Mg:Ti (atomic ratio) being 1:0.05].

Example 4

205.13 g (0.8 mol) of magnesium nitrate hexahydrate, 5.83 g (0.02 mol) of diantimony trioxide and 411.35 g of deionized water were fed into a reactor. Into the mixture thus obtained was added dropwise 423.96 g (0.8 mol) of a 20% aqueous solution of sodium carbonate at 90° C. for 2 hours. After completion of the dropwise addition, the resulting mixture was maintained at 90° C. for 1 hour. That is, it was aged. The mixture containing a precipitate was filtered to remove the mother liquor. Then the precipitate thus recovered was washed with 1-l portions of deionized water 5 times. The precipitate was dried at 90° C. for a day and then fired at 800° C. in a nitrogen atmosphere for 2 hours. Thus an MgO—$Sb_2O_3$ catalyst [Mg:Sb (atomic ratio) being 1:0.05] was obtained.

Example 5

217.95 g (0.85 mol) of magnesium nitrate hexahydrate, 5.24 g (0.0425 mol) of zirconium oxide and 411.35 g of deionized water were fed into a reactor. Into the mixture thus obtained was added dropwise 450.46 g (0.85 mol) of a 20% aqueous solution of sodium carbonate at 90° C. for 2 hours. After completion of the dropwise addition, the resulting mixture was maintained at 90° C. for 1 hour. That is, it was aged. The mixture containing a precipitate was filtered to remove the mother liquor. Then the precipitate thus recovered was washed with 1-l portions of deionized water 5 times. The precipitate was dried at 80° C. for 2 days and then fired at 600° C. in a nitrogen atmosphere for 2 hours. Thus an MgO—$ZrO_2$ catalyst [Mg:Zr (atomic ratio) being 1:0.05] was obtained.

Example 6

The same procedure as that of Example 5 was effected except for using 76.92 g (0.3 mol) of magnesium nitrate hexahydrate, 4.46 g (0.015 mol) of zinc nitrate hexahydrate, 53.24 g of diatomaceous earth, 155.26 g of deionized water and 166.93 g (0.315 mol) of a 20% aqueous solution of sodium carbonate. Thus an MgO—ZnO-diatomaceous earth catalyst [Mg:Zn (atomic ratio) being 1:0.05)] wherein 20% by weight, based on the weight of the diatomaceous earth, of the metal oxides were supported on the diatomaceous earth was obtained.

Comparative Example 1

205.13 g (0.8 mol) of magnesium nitrate hexahydrate and 411.35 g of deionized water were fed into a reactor. Into the mixture thus obtained was added dropwise 423.96 g (0.8 mol) of a 20% aqueous solution of sodium carbonate at 90° C. for 2 hours. After completion of the dropwise addition, the resulting mixture was maintained at 90° C. for 1 hour. That is, it was aged. The mixture containing a precipitate was filtered to thereby remove the mother liquor. Then the precipitate thus recovered was washed with 1-l portions of deionized water 5 times. The precipitate was dried at 90° C. for a day and then fired at 800° C. in a nitrogen atmosphere for 2 hours. Thus an MgO catalyst was obtained.

Comparative Example 2

The same procedure as that of Comparative Example 1 was effected except for using barium nitrate in place of the magnesium nitrate. Thus a BaO catalyst was obtained.

Comparative Example 3

The same procedure as that of Comparative Example 1 was effected except for using a mixture of magnesium nitrate with barium nitrate in place of the magnesium nitrate. Thus an MgO—BaO catalyst [Mg:Ba (atomic ratio) being 1:0.05] was obtained.

Comparative Example 4

128.21 g (0.5 mol) of magnesium nitrate hexahydrate, 9.38 g (0.025 mol) of aluminum nitrate nonahydrate and 259.76 g of deionized water were fed into a reactor. Into the mixture thus obtained was added dropwise 284.85 g (0.5375 mol) of a 20% aqueous solution of sodium carbonate at 90° C. for 2 hours. After completion of the dropwise addition, the resulting mixture was maintained at 90° C. for 1 hour. That is, it was aged. The mixture containing a precipitate was filtered to remove the mother liquor. Then the precipitate thus recovered was washed with 1-l portions of deionized water 5 times. The precipitate was dried at 80° C. for a day and then fired at 600° C. in a nitrogen atmosphere for 2 hours. Thus an MgO—$Al_2O_3$ catalyst [Mg:Al (atomic ratio) being 1:0.05] was obtained.

Comparative Example 5

A composite metal salt KYOWARD 2000 (mfd. by Kyowa Kagaku Kogyo K.K.) was fired at 500° C. for 2 hours. Thus an MgO (59.2%)—$Al_2O_3$ (33%) catalyst was obtained.

The pKa value of each of the catalysts obtained in the above Examples 1 to 6 and Comparative Examples 1 to 5 and the amount of ammonia gas adsorbed to each of the catalysts were measured according to the following methods. Table 1 summarizes the results.

<Method for measuring pKa value>

A 0.1% solution of an indicator in toluene was added to a mixture of 0.1 g of a catalyst (when a supported catalyst was used, it was the weight of the supported catalyst) with 5 ml of toluene, which had been dried with Molecular Sieves, to observe color changes. The indicators employed were those for the judgement of pKa values ranging from 3 to 25, for example, phenolphthalein (pKa: 9.3), 2,4,6-trinitroaniline (pKa: 12.2), 2,4-dinitroaniline (pKa: 15.0), 4-chloro-2-nitroaniline (pKa: 17.2) and 4-nitroaniline (pKa: 18.4).

<Method for determining the amount of ammonia gas adsorbed>

0.5 g of a catalyst (when a supported catalyst was used, it was the weight of the supported catalyst) was packed in a U-shaped column. After evacuating the column at room temperature, an ammonia gas was introduced thereinto until the internal pressure reached 100 Torr. Then the column was maintained as such for several minutes to thereby cause the catalyst to adsorb ammonia. The column was maintained at a temperature of about 60° C. Then the column was evacuated again and heated to 400° C. Based on an increase in pressure due to the ammonia desorbed during the heating, the amount of the ammonia gas adsorbed to the catalyst was calculated.

Reaction Examples 1 to 6 and Comparative Reaction Examples 1 to 5

A 2-l autoclave was charged with 188 g (1 mol) of lauryl alcohol and each of the catalysts obtained in the above Examples 1 to 6 and Comparative Examples 1 to 5 in such a manner as to regulate the amount of the metal oxides to 2% by weight based on the weight of lauryl alcohol. After heating the contents of the autoclave to 165° C., 132 g (3 mol) of ethylene oxide was introduced thereinto at the same temperature while maintaining the pressure at 3 to 5 kg/cm² (gage pressure) to thereby effect a reaction.

After maintaining, i.e., aging, the contents of the autoclave at the same temperature for 1 to 3 hours, they were cooled to 80° C. The reaction product thus obtained was filtered through a filter paper No. 2 (mfd. by Toyo Roshi K.K.) with the use of a pressure filter of 5 cm in inner diameter under a nitrogen pressure of 3 kg/cm² (gage pressure) to thereby eliminate the catalyst.

Table 1 shows the ethylene oxide addition rate (i.e., the number of moles of ethylene oxide absorbed in one hour during the addition reaction) measured according to the method as will be shown hereinbelow, filtering characteristics of the catalyst evaluated in accordance with the criteria as will be shown hereinbelow, and the content of polyethylene glycol formed as a by-product which was separated and determined by GPC analysis.

<Method for measuring the ethylene oxide addition rate>

Ethylene oxide was introduced into an autoclave which had been charged with lauryl alcohol and a catalyst in such an amount as to give an inner pressure of 3 kg/cm² (gage pressure). Then, ethylene oxide was further introduced thereinto in such an amount as to give an inner pressure of 5 kg/cm² (gage pressure). The amount of the ethylene oxide which was used for increasing the pressure from 3 kg/cm² (gage pressure) to 5 kg/cm² (gage pressure) was measured. Then, the addition reaction was effected until the inner pressure would be reduced to 3 kg/cm² (gage pressure). The time required for this addition reaction was measured. The above-mentioned procedure was repeated. The amount of ethylene oxide added per hour during the addition reaction was calculated.

<Criteria for the evaluation of filtering characteristics of the catalyst>

A: requiring at most 1 hour for filtration,

B: requiring 2 to 5 hours for filtration,

C: requiring 5 hours or longer for filtration or elimination of the catalyst by filtration being impossible.

Figure 1:
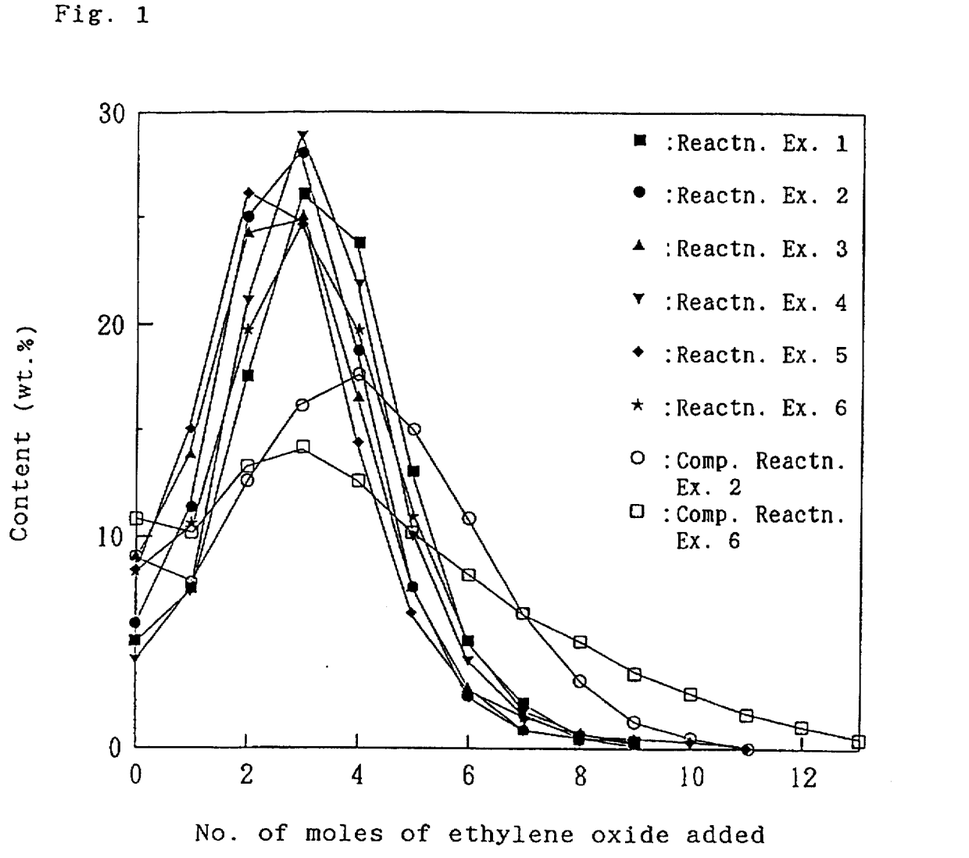
FIG. 1 is a graph which shows the distribution of the number of moles of ethylene oxide added in each of the reaction products obtained in the Reaction Examples 1 to 6 and Comparative Reaction Examples 2 and 6.
Figure 2:
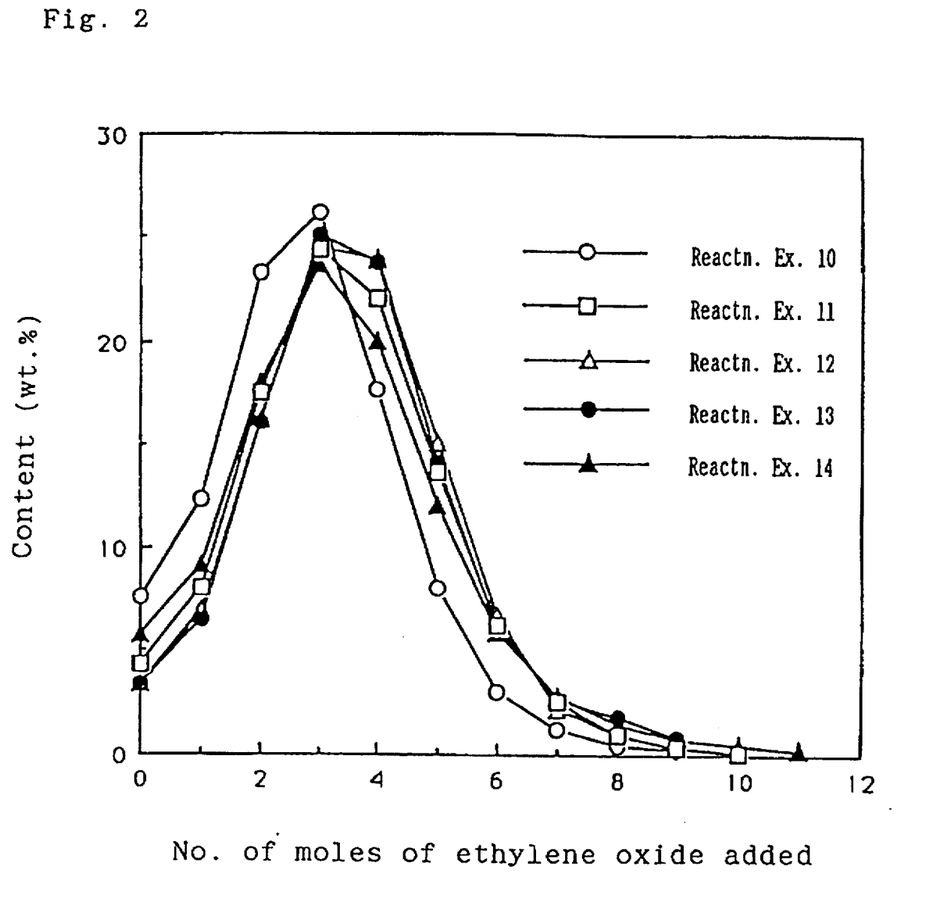
FIG. 2 is a graph which shows the distribution of the number of moles of ethylene oxide added in each of the reaction products obtained in the Reaction Examples 10 to 14.

FIG. 1 shows the results.

The results indicate that the catalysts of the present invention (i.e., the products of Examples 1 to 6) are each excellent in filtering characteristics and that when a catalyst of the present invention is used, a high reaction rate can be achieved while forming little by-products.

As FIG. 1 shows, the distribution of the number of moles of ethylene oxide added in each alkoxylate thus obtained is very sharp as compared with the cases where the comparative catalysts were used.

Examples 7 and 8 and Comparative Example 6

The same procedure as that of Example 1 was effected except for changing the composition ratio of the magnesium nitrate hexahydrate to the zinc nitrate hexahydrate so as to give atomic ratios of magnesium to zinc (i.e., Mg:Zn) of 1:0.01, 1:0.30 and 1:0.50 to thereby give catalysts. Then the pKa value of each catalyst and the amount of ammonia gas adsorbed to each catalyst were measured by the same methods as those described above. Table 2 shows the results.

Reaction Example 7 and 8 and Comparative Reaction Example 7

By using the catalysts obtained in the above Examples 7 and 8 and Comparative Example 6, the same procedure as that of Reaction Example 1 was effected.

The ethylene oxide addition rates and the filtering characteristics of the catalysts were evaluated. Table 2 shows the results.

TABLE 1

| Reactn. Ex. | | Composite metal oxide catalyst | pKa of catalyst | Amt. of NH₃ adsorbed to catalyst μmol/g | Ethylene oxide addn. rate mol/hr | Filtering characteristics of catalyst | Content of by-product (polyethylene glycol) wt. % |
|---|---|---|---|---|---|---|---|
| Reactn. Ex. | 1 | catalyst of Ex. 1 (MgO—ZnO) | 17.2 | 214 | 0.4 | A | 0.1 |
| | 2 | catalyst of Ex. 2 (MgO—SnO) | 17.2 | 304 | 0.4 | B | 0.2 |
| | 3 | catalyst of Ex. 3 (MgO—TiO₂) | 17.2 | 405 | 0.4 | B | 0.3 |
| | 4 | catalyst of Ex. 4 (MgO-Sb₂O₃) | 15.0 | 142 | 2.4 | A | 0.1 |
| | 5 | catalyst of Ex. 5 (MgO—ZrO₂) | 17.2 | 233 | 0.4 | B | 0.1 |
| | 6 | catalyst of Ex. 6 (MgO—ZnO-diatom. earth) | 17.2 | 210 | 1.1 | A | 0.1 |
| Comp. Ex. | 1 | catalyst of Comp. Reactn. Ex. 1 (MgO) | 9.3 | <40 | 0.1 | C | 2.8 |
| | 2 | catalyst of Comp. Ex. 2 (BaO) | 9.3 | <40 | 0.1 | C | 3.4 |
| | 3 | catalyst of Comp. Ex. 3 (MgO—BaO) | 9.3 | <40 | 0.1 | C | 3.2 |
| | 4 | catalyst of Comp. Ex. 4 (MgO—Al₂O₃) | 17.2 | >500 | 0.8 | C | 1.5 |
| | 5 | catalyst of Comp. Ex. 5 (KYOWARD 2000) | — | — | 0.8 | C | 2.8 |

Comparative Reaction Example 6

The same procedure as that of Reaction Example 1 was effected except for using a KOH catalyst (14 by mol based on lauryl alcohol) as the catalyst.

The ethylene oxide addition rate was 0.3 mol/hr or above.

The filtrate of each of the reaction mixtures obtained in the above Reaction Examples 1 to 6 and Comparative Reaction Examples 2 and 6 was subjected to trimethylsilylation and the distribution of number of moles of ethylene oxide added was determined.

The ethylene oxide addition rates were evaluated in accordance with the criteria as will be given hereinbelow, while the filtering characteristics of the catalysts were evaluated in accordance with the same criteria as those described in Reaction Examples 1 to 6.

<Criteria for the evaluation of ethylene oxide addition rate> o: ethylene oxide addition rate ≧ 0.3 mol/hr, x: ethylene oxide addition rate ≦ 0.1 mol/hr.

TABLE 2

| | Atomic ratio of catalyst metals | pKa of catalyst | Amt. of NH₃ adsorbed to catalyst µmol/g | Evaluation of properties | |
|---|---|---|---|---|---|
| | | | | Ethylene oxide addition rate | Filtering characteristics of catalyst |
| Reactn. Ex. 7 | catalyst of Ex. 7<br>Mg : Zn = 1 : 0.01 | 17.2 | 195 | o | A |
| Reactn. Ex. 8 | catalyst of Ex. 8<br>Mg : Zn = 1 : 0.30 | 17.2 | 123 | o | A |
| Comp. Reactn. Ex. 7 | catalyst of Comp. Ex. 6<br>Mg : Zn = 1 : 0.50 | 9.3 | <40 | x | C |

Reaction Example 9

The same procedure as that of Reaction Example 1 was effected except for using the catalyst of Example 4 and 300 g (7 mol) of ethylene oxide.

The ethylene oxide addition rate, the filtering characteristics of the catalyst and the content of the by-product were evaluated each by the same method as the one described in Reaction Examples 1 to 6. Table 3 shows the results.

Comparative Reaction Example 8

The reaction and evaluation of the above Reaction Example 9 were repeated except for using the catalyst of Comparative Example 5. Table 3 shows the results.

TABLE 3

| | Composite metal oxide catalyst | Ethylene oxide addition rate mol/hr | Filtering characteristics of catalyst | Content of by-product (polyethylene glycol) wt. % |
|---|---|---|---|---|
| Reactn. Ex. 9 | catalyst of Ex. 4 (MgO-Sb₂O₃) | 2.1 | A | 0.7 |
| Comp. Reactn. Ex. 8 | catalyst of Comp. Ex. 5 (KYOWARD 2000) | 0.8 | C | 3.5 |

The results given in Table 3 indicate that the catalyst of the present invention is one which is also suitable for the preparation of an alkoxylate with a large number of moles of ethylene oxide added.

Examples 9 and 10

The same procedure as that of Example 4 was effected except for using 148.63 g (2.40 mol) of a 27.5% aqueous ammonia or 320.00 (1.6 mol) of a 20% aqueous solution of NaOH each in place of 423.96 g (0.8 mol) of a 20% aqueous solution of Na₂CO₃ to thereby prepare a catalyst. Then the pKa value and the amount of ammonia gas adsorbed were measured by the same methods as those described above. Table 4 shows the results.

Example 11

The same procedure as that of Example 4 was effected except for using 320.00 g (1.6 mol) of a 20% aqueous solution of NaOH in place of 423.96 g (0.8 mol) of a 20% aqueous solution of Na₂CO₃ and 162.64 g (0.8 mol) of magnesium chloride hexahydrate, in place of 205.13 g (0.8 mol) of magnesium nitrate hexahydrate to thereby prepare a catalyst. Then the pKa value and the amount of ammonia gas adsorbed were measured by the same methods as those described above. Table 4 shows the results.

Example 12

46.66 g (0.8 mol) of magnesium hydroxide, 5.83 g (0.02 mol) of diantimony trioxide and 754 g of deionized water were fed into a reactor. The obtained mixture was stirred at 90° C. for 1 hour and then filtered to thereby eliminate the water. The resulting mixture was dried at 90° C. overnight and then fired at 800° C. for 2 hours in a nitrogen atmosphere. Thus an MgO—Sb₂O₃ catalyst was obtained. Then the pKa value and the amount of ammonia gas adsorbed were measured by the same methods as those described above. Table 4 shows the results.

Example 13

The same procedure as that of Example 11 was effected except for effecting the firing in an air atmosphere to thereby prepare a catalyst. Then the pKa value and the amount of ammonia gas adsorbed were measured by the same methods as those described above. Table 4 shows the results.

Reaction Examples 10 to 14

By using each of the catalysts obtained in the above Examples 9 to 13, a reaction was effected in the same manner as that of Reaction Examples 1 to 6. The ethylene oxide addition rate and the filtering characteristics of the catalyst were evaluated. Table 4 shows the results.

TABLE 4

| Reactn. Ex. | Composite metal oxide catalyst [raw materials of catalyst and precipitant] | pKa of catalyst | Amt. of NH₃ adsorbed to catalyst μmol/g | Ethylene oxide addition rate mol/hr | Filtering characteristics of catalyst | Content of by-product (polyethylene glycol) wt. % |
|---|---|---|---|---|---|---|
| Reactn. Ex. | 10 catalyst of Ex. 9 [Mg(NO₃)₂—Sb₂O₃—NH₃] | 12.2 | 118 | 1.8 | A | 0.3 |
| | 11 catalyst of Ex. 10 [Mg(NO₃)₂—Sb₂O₃—NaOH] | 9.3 | 76 | 4.2 | A | 0.3 |
| | 12 catalyst of Ex. 11 [MgCl₂—Sb₂O₃—NaOH] | 12.2 | 61 | 7.2 | A | 0.2 |
| | 13 catalyst of Ex. 12 [Mg(OH)₂—Sb₂O₃] | 9.3 | 93 | 2.4 | A | 0.5 |
| | 14 catalyst of Ex. 5 [MgCl₂—Sb₂O₃—NaOH] | 12.2 | 60 | 1.5 | A | 0.5 |

The results given in Table 4 indicate that the catalysts of the present invention each shows a high activity and excellent filtering characteristics, though they differ from each other in the catalyst materials.

We claim:

1. An alkoxylation catalyst comprising magnesium oxide and a second oxide of at least one element selected from the group consisting of the group 2B elements, the group 4A elements, the group 4B elements, and the group 5B elements and the group 6A elements in the periodic table of the subgroup system, in proportions wherein the catalyst has a basicity point expressed in pKa value from 9 to 25 and an acidity point expressed in the amount of ammonia gas adsorbed from 50 to 500 μmol/g.

2. The alkoxylation catalyst as set forth in claim 1, wherein said second oxide is at least one member selected from the group consisting of oxides of zinc, antimony, tin, titanium and zirconium.

3. The alkoxylation catalyst as set forth in claim 1, wherein said second oxide is an oxide of antimony.

4. The alkoxylation catalyst as set forth in claim 1, which contains from 0.005 to 0.4 atom, per atom of magnesium, of at least one element selected from the group consisting of the group 2B elements, the group 4A elements, the group 4B elements, the group 5B elements and the group 6A elements in the periodic table of the subgroup system.

5. The alkoxylation catalyst as set forth in claim 1, which is supported on a support.

6. A process for the preparation of an alkoxylation catalyst having a basicity point expressed in pKa value from 9 to 25 and an acidity point expressed in the amount of ammonia gas adsorbed from 50 to 500 μmol/g, which comprises coprecipitating a water-soluble or water-dispersible magnesium compound with a water-soluble or water-dispersible compound containing at least one element selected from the group consisting of the group 2B elements, the group 4A elements, the group 4B elements, the group 5B elements and the group 6A elements in the periodic table of the subgroup system and firing the precipitate thus obtained.

7. The process for the preparation of an alkoxylation catalyst as set forth in claim 6, wherein said water-soluble or water-dispersible magnesium compound is magnesium nitrate, magnesium chloride or magnesium hydroxide.

8. The process for the preparation of an alkoxylation catalyst as set forth in claim 6, wherein said water-soluble or water-dispersible compound is an oxide of antimony.

9. The process for the preparation of an alkoxylation catalyst as set forth in claim 6, wherein the coprecipitation is effected with the use of aqueous ammonia or an aqueous solution of sodium hydroxide.

10. A process for preparing an alkoxylate which comprises conducting a reaction for adding an alkylene oxide to a compound containing an active hydrogen atom(s) in the presence of an alkoxylation catalyst comprising magnesium oxide and a second oxide of at Least one element selected from the group consisting of the group 2B elements, the group 4A elements, the group 4B elements, and the group 5B elements and the group 6A elements in the periodic table of the subgroup system, in proportions wherein the catalyst has a basicity point expressed in pKa value from 9 to 25 and an acidity point expressed in the amount of ammonia gas adsorbed from 50 to 500 μmol/g.

11. The process for preparing an alkoxylate as set forth in claim 10, wherein said compound containing an active hydrogen atom(s) is a linear or branched, saturated or unsaturated alcohol having 8 to 22 carbon atoms.

* * * * *